(12) United States Patent
Milton et al.

(10) Patent No.: US 8,931,181 B2
(45) Date of Patent: Jan. 13, 2015

(54) SCALPEL BLADE SAFETY ACCESSORY

(75) Inventors: Trevor John Milton, Western Cape (ZA); Norman Anthony Nieuwenhuizen, Gauteng (ZA)

(73) Assignee: Medi-Safe Surgicals (Pty) Ltd, Somerest West, Western Cape Province (ZA)

( * ) Notice: Subject to any disclaimer, the term of this patent is extended or adjusted under 35 U.S.C. 154(b) by 0 days.

(21) Appl. No.: 14/000,505

(22) PCT Filed: Jul. 16, 2012

(86) PCT No.: PCT/IB2012/053631
§ 371 (c)(1),
(2), (4) Date: Aug. 20, 2013

(87) PCT Pub. No.: WO2013/041982
PCT Pub. Date: Mar. 28, 2013

(65) Prior Publication Data
US 2013/0331871 A1    Dec. 12, 2013

(30) Foreign Application Priority Data

Sep. 23, 2011  (ZA) ................................. 2011/06969
Feb. 24, 2012  (ZA) ................................. 2012/01376

(51) Int. Cl.
*A61B 17/32*     (2006.01)
*A61B 17/3213*   (2006.01)
*A61B 17/3211*   (2006.01)

(52) U.S. Cl.
CPC ... *A61B 17/3213* (2013.01); *A61B 2017/32113* (2013.01)
USPC ........................................... 30/162; 606/167

(58) Field of Classification Search
USPC ..................................... 30/151, 162; 606/167
See application file for complete search history.

(56) References Cited

U.S. PATENT DOCUMENTS

| 5,527,329 | A | * | 6/1996 | Gharibian ..................... 606/167 |
| 5,868,771 | A | * | 2/1999 | Herbert et al. ................ 606/167 |
| 5,919,201 | A | * | 7/1999 | Carter et al. .................. 606/167 |

(Continued)

FOREIGN PATENT DOCUMENTS

WO          2009/074863 A2    6/2009
WO    WO 2013/041982 A3  *  3/2013

OTHER PUBLICATIONS

International Search Report and Written Opinion of the International Searching Authority from the International Bureau of WIPO for International Application No. PCT/IB2012/053631, dated Jan. 28, 2013, 6 pages.

*Primary Examiner* — Hwei C Payer
(74) *Attorney, Agent, or Firm* — Fitch Even Tabin & Flannery, LLP (57) ABSTRACT

A scalpel blade accessory and cartridge are provided wherein a tubular guard is slidable over the scalpel blade carrier between a retracted position in which the blade carrier is positioned to expose any scalpel blade associated with it for use and an extended position in which the guard covers the blade carrier and any blade thereon. The scalpel blade has a mounting slot for attachment to a lug on a standard scalpel handle for use. The blade carrier has a bridge spanning an alignment face so as to provide space for a scalpel blade between the alignment face and bridge. A blade catch cooperates with a rear end of the mounting slot to hold a relevant scalpel blade captive. The blade catch is disengagable by assembling it onto a standard handle, in use.

14 Claims, 5 Drawing Sheets

(56) References Cited

U.S. PATENT DOCUMENTS

| | | | |
|---|---|---|---|
| 5,938,676 A | 8/1999 | Cohn et al. | |
| 6,053,929 A * | 4/2000 | Cohn et al. | 606/167 |
| 6,629,985 B1 * | 10/2003 | Kiehne | 606/167 |
| 7,172,611 B2 * | 2/2007 | Harding et al. | 606/167 |
| 7,857,824 B2 * | 12/2010 | Kiehne | 606/167 |
| 7,900,362 B2 * | 3/2011 | Djordjevic et al. | 30/162 |
| 8,015,712 B2 * | 9/2011 | Yi et al. | 30/162 |
| 8,567,072 B2 * | 10/2013 | Yi et al. | 30/162 |
| 2002/0143352 A1 * | 10/2002 | Newman et al. | 606/167 |
| 2006/0095057 A1 | 5/2006 | Yi et al. | |
| 2006/0100650 A1 * | 5/2006 | Kiehne | 606/167 |
| 2006/0212058 A1 * | 9/2006 | Djordjevic et al. | 606/167 |
| 2010/0036404 A1 * | 2/2010 | Yi et al. | 606/167 |
| 2012/0245610 A1 * | 9/2012 | Hajgato et al. | 606/167 |
| 2013/0079804 A1 * | 3/2013 | Milton et al. | 606/167 |
| 2013/0331871 A1 * | 12/2013 | Milton et al. | 606/167 |

* cited by examiner

SCALPEL BLADE SAFETY ACCESSORY

CROSS-REFERENCE TO RELATED APPLICATIONS

This application is a U.S. national phase application filed under 35 U.S.C. §371 of International Application PCT/IB2012/053631, filed on Jul. 16, 2012, designating the United States, which claims priority from South African Application No. 2011/06969, filed on Sep. 23, 2011, and South African Application No. 2012/01376, filed on Feb. 24, 2012, which are hereby incorporated herein by reference in their entirety.

FIELD OF THE INVENTION

This invention relates to an accessory for a scalpel blade (sometimes referred to as a surgical knife) of a generally disposable nature and of the type including a scalpel blade carrier and a guard for covering a scalpel blade that in use is installed on the blade carrier. The guard is movable relative to the blade carrier between an extended position in which it covers a scalpel blade fitted to the blade carrier and scalpel handle during periods of non-use of the scalpel and a retracted position in which the scalpel blade is exposed for use.

More particularly, the invention relates both to a scalpel blade accessory that can be supplied as such without a scalpel blade attached to the blade carrier and to a scalpel blade accessory that has a blade fitted to it in which instance the accessory and blade combination may be regarded as a scalpel blade cartridge. In either event, a scalpel blade accessory according to this invention may be considered to be a single procedure disposable item.

BACKGROUND TO THE INVENTION

Disposable scalpels that have a blade and an injection moulded plastic handle are available in both a simple and a retractable safety configuration. However, many surgeons find such disposable scalpels too light in weight and prefer to use a scalpel having a heavier re-usable stainless steel handle and a replaceable disposable blade.

A rather common form of scalpel has a stainless steel handle with a longitudinally extending blade-supporting stem at one end that merges with a terminal elongated blade engaging lug carried by the stem with the lug being adapted to cooperate with a longitudinal slot in a scalpel blade. The slot in the scalpel blade has a wider proximal region nearer the handle through which the lug can pass obliquely and a narrower forward region further from the handle having inner edges slidably engaging in accommodating grooves in two opposite side surfaces of the lug. Such a scalpel will, in this specification, be referred to as a standard scalpel; such a handle will be referred to as a standard scalpel handle; and such a blade will be referred to as a standard scalpel blade. Such standard handles are, as far as applicant is aware, generally made in two different sizes, but the same type of attachment may also be made in custom sizes depending on the requirements of a manufacturer and any custom made scalpels, handles and blades are intended to be included within the definition of "standard".

The free proximal end edge of a standard scalpel blade may be angled to the length of the blade and co-operates with a positioning shoulder on the handle that acts as an abutment in the assembled condition. The standard blade is thus firmly held in interlocking connection with the handle and the angled proximal end of the blade needs to be flexed away from the handle in order to release the blade from the lug. A variety of different blade removing accessories are available.

It is widely recognized that it is generally desirable for a scalpel to be provided with a guard that can be used to cover the scalpel blade when it is not in use; to expose the scalpel blade when it is required for use; and, as may be appropriate, to contain the scalpel blade for disposal purposes.

A guard that is slidable forwards and rearwards on a specially custom made stainless steel scalpel handle that is different from that described above is described in each of patent publications DE20310905; EP05551965, US20100063522 and WO03099145.

U.S. Pat. No. 5,868,771 describes a similar arrangement of a specially made stainless steel scalpel handle that utilizes a standard blade mounting stem although it does require a special shape of blade having a proximal end bent out of the plane of the rest of the blade.

Applicant is only aware of two commercially available scalpel blade cartridge systems and both of these use custom made stainless steel handles with the result that the cartridges cannot be used with any other handle. Neither can be used with a standard scalpel handle a standard scalpel blade cannot be used with those specially made handles.

At least in most cases in which a blade guard is slidable relative to the handle, the handle is shaped to provide suitable guides for cooperation with the blade guard.

Patent publication WO2008077084, on the other hand, describes an arrangement in which a scalpel blade cartridge comprises two parts, namely a blade carrier to which the scalpel blade is attached and that is a separate part from a stainless steel scalpel handle. A blade guard that is stationary relative to the scalpel handle is provided. The blade carrier slides relative to the handle and blade guard assembly so as to cause the blade to project beyond the end of the guard, as may be required for use, or to be retracted within the confines of the guard. Apart from the fact that a specially made custom stainless steel handle needs to be manufactured, applicant believes that the blade being supported exclusively by a blade carrier that is a separate part with respect to the handle, and therefore only indirectly by the handle itself, may invite a situation in which the indirect attachment of the blade to the handle results in unwanted play.

The difficulty created by the requirement of custom made stainless steel handles is the fact that they represent what is very often an unacceptable additional cost whereas there are numerous standard stainless steel handles in medical facilities throughout the world that are available for use. Also, there are numerous different shapes and sizes of standard blades made of different steels that are available at medical facilities that can be attached to a standard stainless steel scalpel handle but not to any of the custom-made handles.

In addition, all existing scalpel blade cartridges of which applicant is aware are fitted with stainless steel scalpel blades. There are, however, surgeons that prefer to use carbon steel scalpel blades. However, carbon steel scalpel blades are not presently available in a cartridge format because of their tendency to rust or corrode unless special protection is afforded the surfaces of such blades. At the present time such protection is inconsistent with a carbon steel blade being supplied in a cartridge format.

There is thus a need for a scalpel blade accessory that can be used for the disposal of used scalpel blades individually enclosed within a guard and an accessory that can be used in conjunction with either stainless steel or carbon steel scalpel blades, if required, at least under particular circumstances.

There is also a need for an accessory that enables standard scalpel handles to be employed in a manner having enhanced safety.

It should be noted that this specification uses the term tubular guard for a guard that is intended to substantially encircle a scalpel blade for protective and disposal purposes and is not intended to imply that the specification is limited to the tube being continuous in the peripheral direction.

SUMMARY OF THE INVENTION

In accordance with a first aspect of this invention there is provided a scalpel blade accessory comprising a scalpel blade carrier and a tubular guard slidable over the scalpel blade carrier between a retracted position in which the blade carrier is positioned to expose any blade associated with it for use and an extended position in which the guard covers the blade carrier and any such blade, the scalpel blade carrier being configured for receiving in cooperating relationship a standard scalpel blade for attachment to a standard scalpel handle for use, wherein the scalpel blade carrier has an alignment face for cooperation with a side face of a blade and at least one opening providing access through the alignment face to a position corresponding to that in which a mounting slot of any scalpel blade is to be located when a blade is attached to the blade carrier, wherein the blade carrier has a bridge spanning the alignment face so as to provide space for a scalpel blade between the alignment face and bridge and wherein the bridge supports a blade catch positioned to cooperate with a rear end of a mounting slot of a scalpel blade to hold a relevant scalpel blade captive relative to the blade carrier in the absence of any scalpel handle, the blade catch and alignment face being such that the blade catch is disengagable from a position corresponding to registration with the rear end of the mounting slot of a scalpel blade consequent on engagement between the blade and a lug of a standard scalpel handle when the blade carrier and a blade carried thereby are assembled onto such a handle, in use.

Further features of the first aspect of the invention provide for the blade catch to be moulded integral with the bridge and to be located at the end of an arm extending at right angles to the bridge in the general direction of movement of the blade carrier relative to the tubular guard; for the cross-sectional shape of the blade carrier and tubular guard to provide a stop that limits movement of the tubular guard relative to the blade carrier in the direction corresponding to retraction of the guard relative to the blade carrier; and for a limit catch on either the blade carrier or tubular guard to co-operate with a formation on the tubular guard or blade carrier, as the case may be, to limit movement of the blade carrier relative to the tubular guard in the opposite direction being that corresponding to the extended position in which the tubular guide covers the blade carrier.

Still further features of the invention provide for a manually releasable locking catch to be provided on the tubular guard with a cooperating notch being provided on the blade carrier to releasably lock the tubular guard relative to the blade carrier in a position in which the tubular guard is fully extended and covers the blade carrier and any blade carried thereby; for the same manually releasable locking catch to be such that the locking catch is urged into tighter engagement with the notch during the application of longitudinal force to the blade carrier such as may be occasioned by the installation of a scalpel blade that is already installed in the accessory onto the lug of a standard scalpel handle.

Additional features of the invention provide for the rear end region of the blade carrier to be provided with a laterally movable release member for operatively urging the rear end of the blade carrier and thus any blade carried by it out of engagement with a lug of a supporting scalpel handle in order to remove the blade and accessory therefrom; for the release member to be configured such that its rear end in the fully retracted condition of the tubular guard on the blade carrier is in cooperating relationship with a manually operable stop located on one side of the tubular guard wherein the stop can be urged against a resiliency that biases it to its normal relaxed condition, to cooperate with the rear end of the release member and prevent it from moving rearwards relative to the tubular guard; and for the release member at its forward end to cooperate with a reduced size of passage within the tubular guard constituting a change in the cross-sectional shape of the blade carrier and tubular guard to provide a stop limiting relative movement of the tubular guard relative to the blade carrier in a direction corresponding to retraction of the tubular guard relative to the blade carrier.

Yet further features of the invention provide for the blade carrier to have a slightly inclined rear support face forming part of the alignment face and configured to cooperate with the rear end of a scalpel blade to flex the rear end of the blade slightly in a direction away from the access face thereof in a manner that will still allow the rear end of the slot of a standard scalpel blade to cooperate with a lug of a standard scalpel handle, in use; for the terminal end of the rear support face to have a transverse stop for cooperation with a rear end of a scalpel blade, in use, the stop typically being angled relative to the length of a standard scalpel blade; for a holding catch to be formed between the blade carrier and guard for holding the guard in a retracted position in which the blade carrier is in a position corresponding to a blade being exposed for use; and for the blade carrier and guard to have co-operating grooves and rails for guiding movement of the guard relative to the blade carrier with the blade carrier in substance supporting the guard.

In accordance with a second aspect of the invention there is provided a scalpel blade cartridge comprising a scalpel blade accessory having a scalpel blade carrier receiving in co-operating relationship a standard scalpel blade for attachment to a standard scalpel handle for use and a tubular guard slidable over the scalpel blade carrier between a retracted position in which the blade carrier is positioned to expose the scalpel blade associated with it for use and an extended position in which the guard covers the blade carrier and scalpel blade, wherein the scalpel blade carrier has an alignment face for cooperation with a side face of the scalpel blade and at least one opening providing access through the alignment face to a mounting slot provided in the scalpel blade, wherein the blade carrier has a bridge spanning the alignment face so as to accommodate a scalpel blade between the alignment face and bridge and wherein the bridge supports a blade catch positioned to cooperate with a rear end of the mounting slot of the scalpel blade to hold the scalpel blade captive relative to the blade carrier in the absence of any scalpel handle, wherein the blade catch and alignment face are such that the blade catch is disengagable from a position corresponding to registration with the rear end of the mounting slot of the scalpel blade consequent on engagement between the blade and a lug of a standard scalpel handle when the blade carrier and scalpel blade carried thereby are assembled onto such a handle, in use.

As regards the disengagement of the blade catch during installation of a scalpel blade accessory and blade in a cartridge form on a standard scalpel handle, this may take place consequent on a straightening of a formerly bowed section of the blade in the uninstalled condition; or it may take place consequent on the lug of the handle urging the blade catch out of engagement with the slot, or it may be a combination of actions.

The present invention therefore provides a scalpel blade accessory that may be supplied as such into the market and may be used by individual surgeons to install, or have installed, their own choice of scalpel blades as and when required.

A scalpel blade accessory as provided by this invention may also be packaged together with a scalpel blade that may be in a separate packaging such as may be necessary from the point of view of maintaining adequate corrosion protection of a carbon steel scalpel blade, or any other scalpel blade that may be susceptible to corrosion.

On the other hand, the scalpel blade accessory may be fitted with a scalpel blade at a suitable fitments centre, optionally the factory producing the scalpel blade accessory; or a site at which scalpel blades are produced; or a site at which scalpel cartridges are simply assembled for marketing into the marketplace.

Still further, the scalpel blade accessory provided by this invention may be employed with the main object of its use being as a safety disposal device when a scalpel blade has served its purpose.

There are thus a number of different ways in which a scalpel blade accessory according to the invention can be employed.

In order that the above and other features of the invention may be more fully understood, one embodiment of scalpel blade accessory according to the invention and scalpel blade cartridge embodying same will now be described with reference to the accompanying drawings.

DETAILED DESCRIPTION WITH REFERENCE TO THE DRAWINGS

In the following description, for ease of understanding, much of the description will relate to the scalpel blade accessory with a standard scalpel blade in position and its relationship with a standard scalpel handle. It will, however, be understood that the accessory itself without a blade is an important article of merchandise according to the present invention as is a scalpel blade cartridge that consists of a scalpel blade accessory according to the invention that is preloaded with a scalpel blade, typically in that instance a stainless steel scalpel blade.

Figure 1:
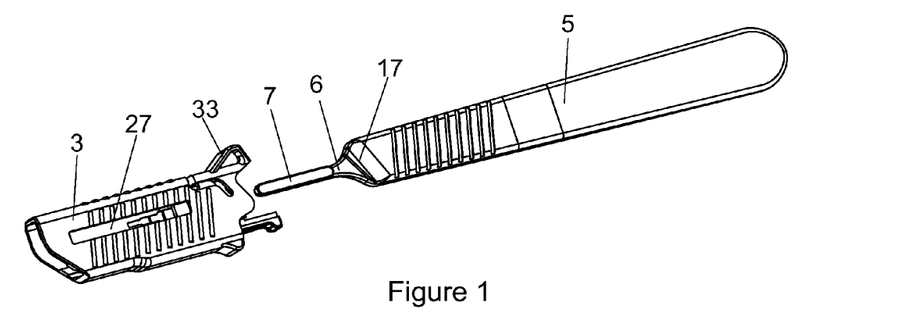
FIG. 1 is an exploded three-dimensional view from one side in a forward position illustrating one embodiment of scalpel blade cartridge including a scalpel blade accessory according to the invention in exploded relationship relative to a standard scalpel handle.
Figure 2:
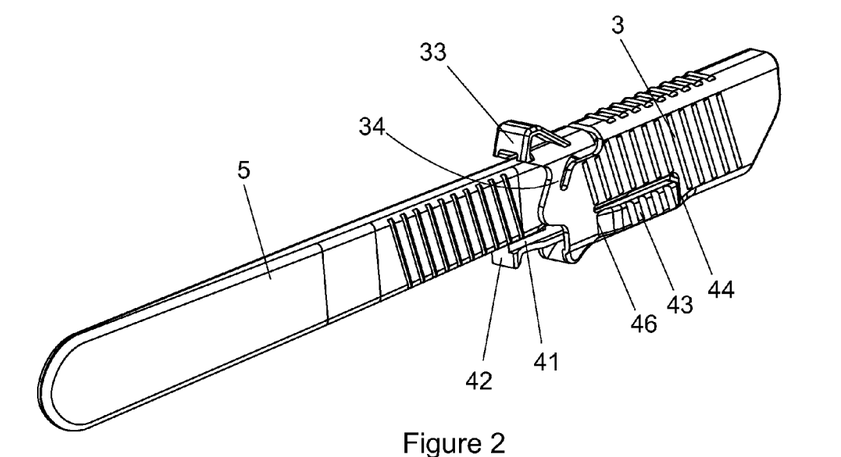
FIG. 2 is a three-dimensional view from an offset rear position on the other side of the handle showing the scalpel blade cartridge in the installed position.
Figure 3:
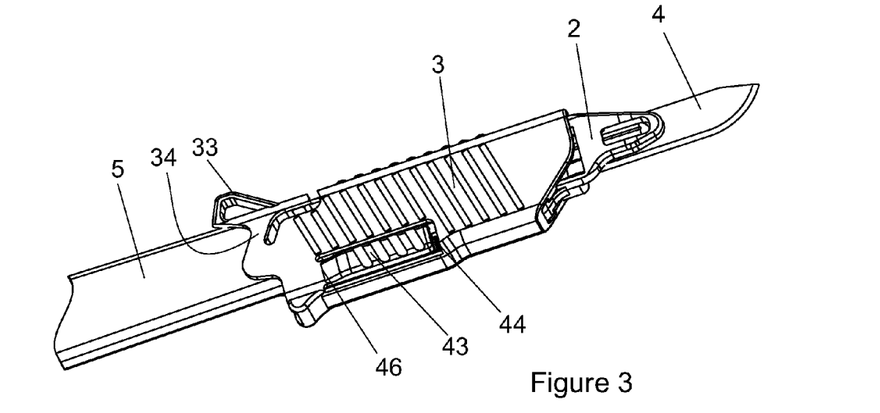
FIG. 3 is a three-dimensional view from an offset forward position on the same side of the handle as is shown in FIG. 2 and showing the tubular guard in a retracted position and the scalpel blade correspondingly exposed.
Figure 12:
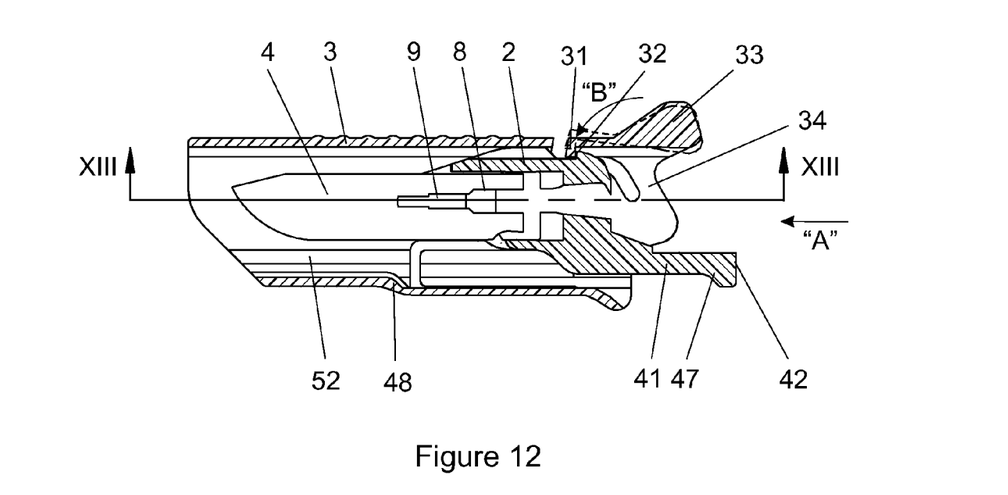
FIG. 12 is the same as FIG. 11 but with a blade in the installed position.
Figure 13:
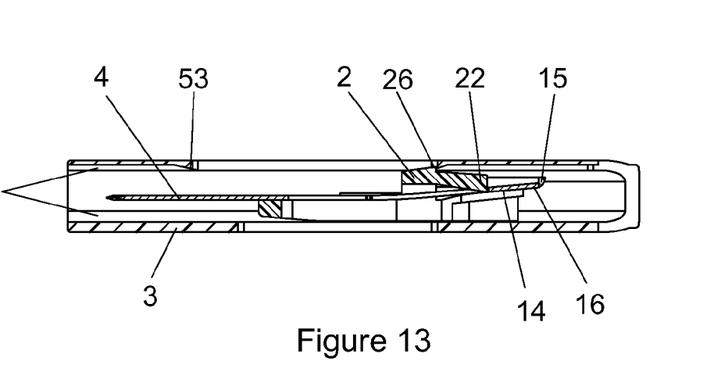
FIG. 13 is a sectional plan view of a scalpel blade cartridge assembly taken along the line XIII to XIII in FIG. 12; and, FIG. 14 is a side elevation thereof showing the tubular guard in the retracted condition with the blade consequently exposed for use.
Figure 14:
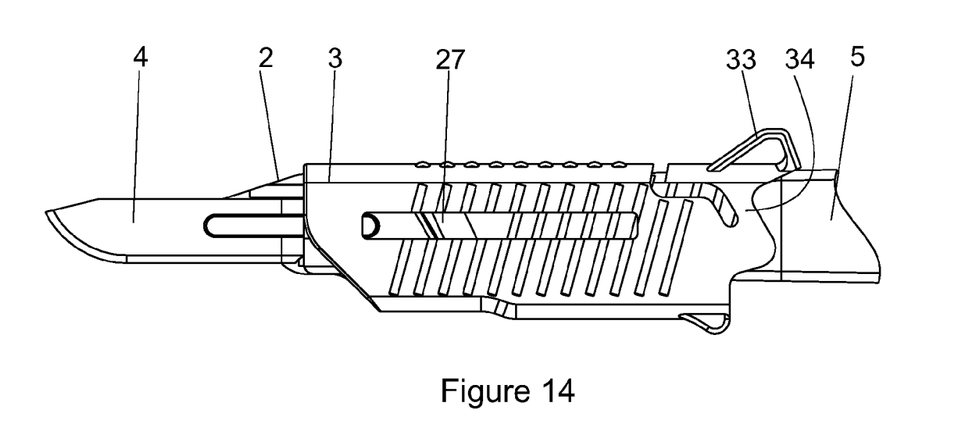

In the embodiment of the invention illustrated in the drawings, a scalpel blade accessory comprises a moulded plastics scalpel blade carrier (2) and a moulded plastics tubular guard (3) that is slidable over the scalpel blade carrier between a retracted position that is shown in FIGS. 3 and 14 in which the blade carrier is positioned to expose, for use, a standard scalpel blade (4) with which it is associated and an extended position that is shown in FIGS. 2 and 12 in which the guard covers and fully encircles the blade.

As indicated in the preamble to this specification a standard scalpel (within the meaning of this specification) comprises a standard stainless steel handle (5) with a longitudinally extending blade-supporting stem (6) at one end that merges with an elongated blade engaging lug (7) carried by the stem. The lug is adapted to cooperate with a longitudinal mounting slot in a scalpel blade which has a wider rear region (8) that is operatively nearer the handle and through which the lug can pass obliquely. A narrower forward region (9) of the mounting slot has inner edges slidably engagable in accommodating grooves (11) (see FIGS. 8 and 9) in two opposite generally parallel side surfaces of the lug. This arrangement provides an extremely firm attachment between a standard scalpel blade and a standard scalpel handle.

The scalpel blade carrier in this embodiment of the invention has an alignment face (12) for cooperation with a side face of a blade and at least one opening (13) providing access for the lug of a standard scalpel handle through the alignment face to a position corresponding to that in which the mounting slot of a scalpel blade is located when the blade is attached to the blade carrier. The alignment face has a slightly inclined rear support face (14) cooperating in use with the rear end region of a blade to flex, in use, the rear end of the blade slightly in a direction away from the access face thereof whilst still allowing the rear end of the slot to cooperate with a lug of a scalpel handle on which the cartridge is installed.

The rearmost end of the rear support face of the blade carrier has a transverse stop (15) that is angled at the same angle as the end (16) of a standard scalpel blade in order to locate the end of the blade. The rear end of the blade carrier itself is arranged to co-operate with a positioning shoulder (17) on the handle that acts as an abutment in the operative condition.

Figure 5:
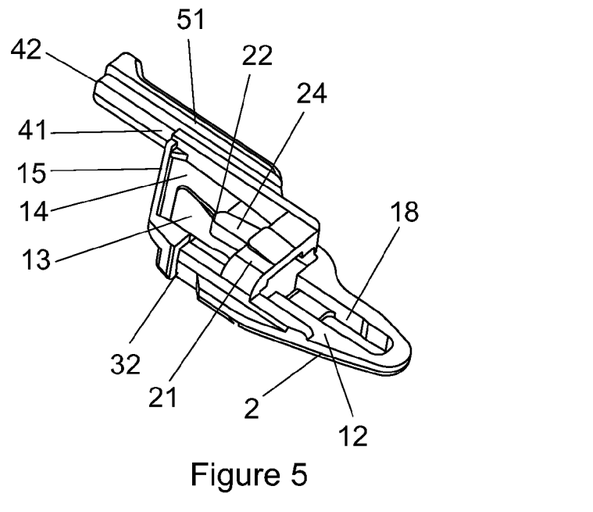
FIG. 5 is a three-dimensional view of the blade carrier alone from the opposite side and front thereof.
Figure 5A:
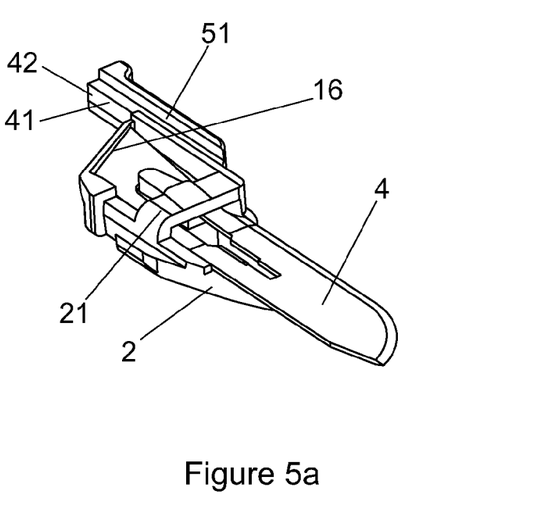
FIG. 5a is the same but showing a blade in situ in the blade carrier.

A recess (18) (see FIG. 5) in the alignment face neatly accommodates the lug of a handle, in use.

The blade carrier has an integral bridge (21) spanning the alignment face so as to provide space for the scalpel blade between the alignment face and bridge. The bridge supports a blade catch (22) positioned to cooperate with a rear end (23) of the mounting slot of a scalpel blade to hold it captive relative to the blade carrier in the absence of any scalpel handle.

The blade catch is moulded integral with the bridge and is located at the free end of an arm (24) that extends at right angles to the bridge in a generally rearward direction corresponding to the direction of movement of the tubular guard relative to the blade carrier. The plastic material from which the blade carrier is moulded and its design are such that the blade catch may be movable to a limited extent laterally from a position corresponding to registration with the rear end of the mounting slot of a scalpel blade.

Figure 7:
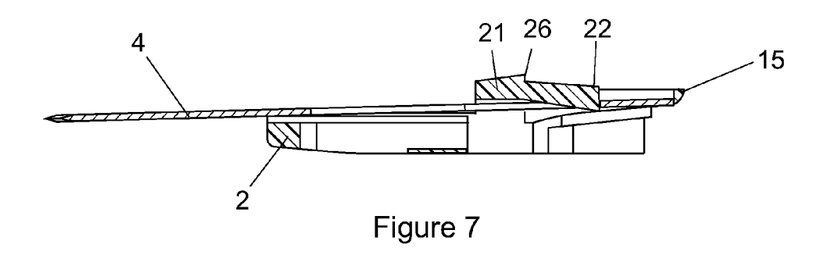
FIG. 7 is a sectional plan view of the blade and blade carrier alone.
Figure 8:
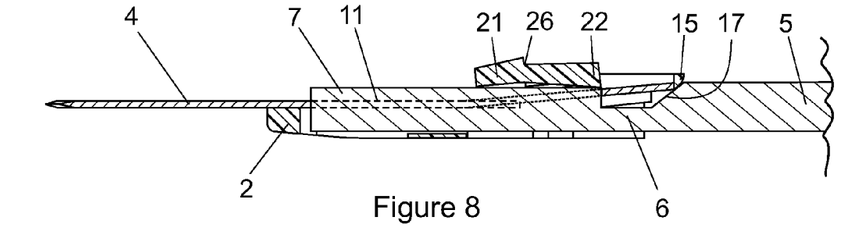
FIG. 8 is the same as FIG. 7 but showing the lug of a standard scalpel handle installed relative thereto with the blade catch disengaged from the blade.
Figure 9:
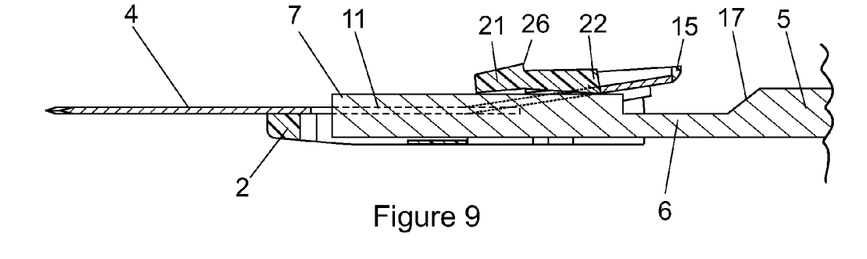
FIG. 9 is the same as FIG. 7 but showing the disengagement of the blade and blade carrier from the lug of the standard scalpel handle to remove the cartridge from the handle.
Figure 10:
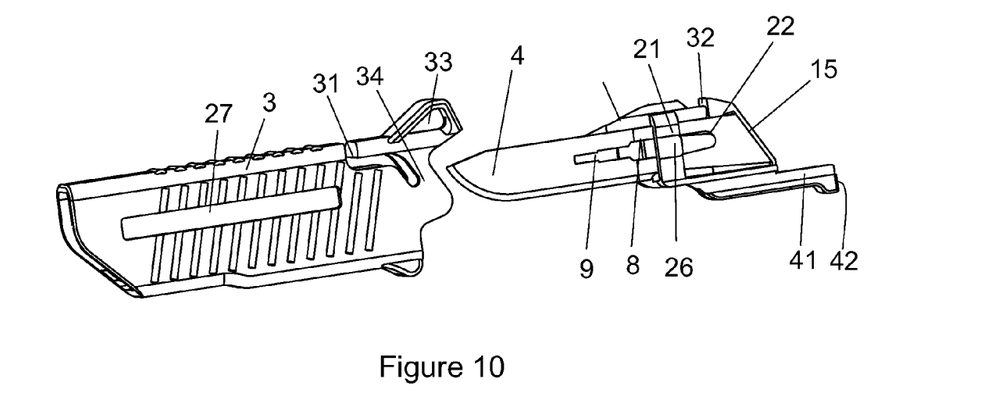
FIG. 10 illustrates the assembly of a blade mounted on a blade carrier being inserted into the tubular guard.

FIG. 7 of the drawings illustrates the position of a scalpel blade installed on the blade carrier before the blade is mounted on a standard scalpel handle. FIG. 8 illustrates the lug of a standard scalpel handle in the installed position in which the blade catch is out of registration with the end of the slot of the blade. The disengagement of the blade catch during installation of a scalpel blade in a cartridge on a standard scalpel handle may take place consequent on a straightening by the rigid lug of the handle of a forward section of the blade with a consequent flexing of the rear section thereof as a result of the terminal end of the blade bearing against the inclined rear support face of the blade carrier. It may, in the alternative, take place consequent on the lug of the handle urging the blade catch out of engagement with the slot, but is most likely a combination of these two actions. Whatever the action, the result is that the scalpel blade is firmly attached to the lug of the standard scalpel handle in the installed condition and the blade carrier is held firmly relative to the handle.

On the outside surface of the bridge is an integral limit catch (26) that co-operates with an end of a slot (27) extending along the side of the tubular guard to limit movement of the blade carrier relative to the tubular guard in the direction corresponding to the extended position in which the tubular guide covers the blade carrier. This limit catch is configured so that it automatically snaps into cooperation with the slot when the blade carrier is initially installed in the tubular guard.

Figure 11:
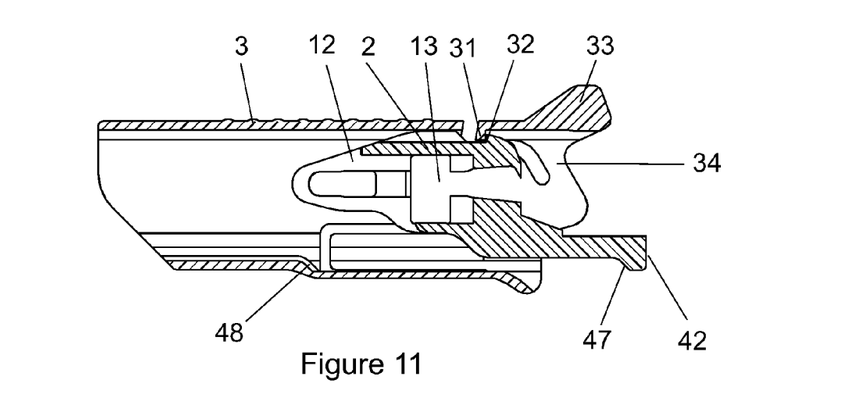
FIG. 11 is a sectional elevation of the scalpel blade accessory without a blade from the side to which the alignment face is directed.

As shown most clearly in FIGS. 11 and 12, an integral manually releasable locking catch (31) is provided on the tubular guard with a cooperating notch (32) being provided on the blade carrier to releasably lock the tubular guard relative to the blade carrier in a position in which the tubular guard is fully extended and covers the blade. The locking catch is carried by a manually operable button (33) that is connected to the main body of the tubular guard by slightly sinuous connecting zones (34) that allow the locking catch to lift out of the notch when the button is operated. By exerting a generally rearward and downward pressure on the button, the locking catch can be released by moving upwards to enable the guard to be slid rearwards to a position in which it covers the adjacent part of the handle and exposes the blade for use. This movement is achieved by a flexing of the integral connecting zones and the positions of the button and catch into the disengaging action are shown in dotted lines in FIG. 12.

The arrangement is, however, such that the locking catch is urged into tighter engagement with the notch during the application of longitudinal force to the blade carrier such as may be occasioned by a scalpel blade that is in the accessory being installed onto the lug of a standard scalpel handle. The notch has a cooperating wall that, when a force is exerted on the blade carrier in the direction indicated by arrow "A", the catch is urged towards rotation in a direction indicated by arrow "B", that is, into firmer engagement with the notch. The notch and locking catch are designed so that increased force on the blade carrier that is occasioned by installing what is in effect a blade cartridge on a standard scalpel handle simply serves to lock the blade carrier within the tubular guard more firmly.

The rear end region of the blade carrier is extended rearwards to define an integral laterally movable release member (41) for operatively urging the rear end of the blade carrier and any blade carried by it out of engagement with a lug of a supporting scalpel handle in order to remove the blade and accessory (blade cartridge) therefrom.

The release member is also configured such that in the fully retracted condition of the tubular guard on the blade carrier that corresponds to the fully exposed condition of a blade carried by the blade carrier, its rear end (42) is in cooperating relationship with a manually operable stop (43) located on one side of the tubular guard. The manually operable stop is formed by a distal end (44) of an integral linear locking element located on one side of the tubular guard that can be urged against the natural resiliency of the wall of the tubular guard that biases it to its normal relaxed condition, to cooperate with the rear end of the release member and thereby prevent it from moving rearwards relative to the tubular guard. The locking element is integral with the tubular guard at its proximal end (46). The locking element preferably stands at least slightly proud of the side surface of the tubular guard in a position in which it is convenient for a surgeon to depress it whilst urging the scalpel blade into a patient with a type of stabbing movement without the blade being allowed to move rearwards relative to the tubular guard.

A further function of the release member is for its forward end (47) to be arranged to cooperate with a stop (48) formed by a reduced size of passage within the tubular guard to define the full extent of exposure of the blade in use with the tubular guard fully retracted. This arrangement allows the scalpel blade to be fully exposed with the tubular guard fully retracted. This effectively provides a stop that limits relative movement of the tubular guard relative to the blade carrier in the direction corresponding to retraction of the guard relative to the blade carrier.

Figure 4:
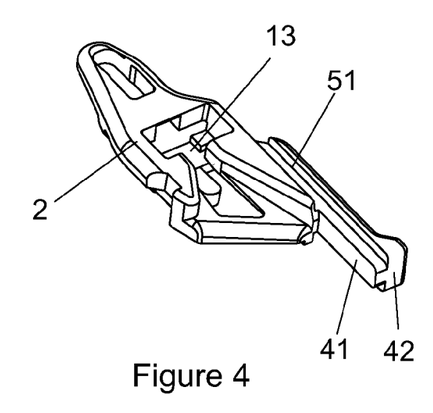
FIG. 4 is a three-dimensional view of the blade carrier alone from the rear and access side thereof.
Figure 4A:
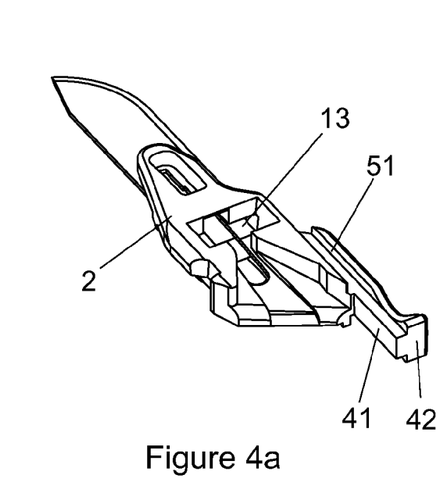
FIG. 4a is the same but showing a blade in situ in the blade carrier.
Figure 6:
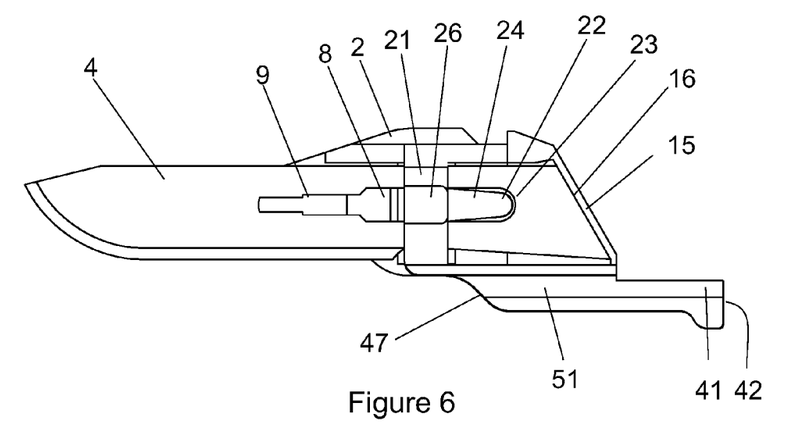
FIG. 6 is a side elevation of the blade carrier from the side opposite the access side thereof with a blade in situ.

The blade carrier has, offset from the alignment face (12), longitudinally extending grooves (51) (see in particular FIGS. 4 to 6) that extend along the sides of the laterally movable release member (41) and serve to guide the tubular guard for longitudinal movement.

The tubular guard (3) has rails (52) that cooperate with the grooves (51) in the blade carrier so that the tubular guard can slide over the scalpel blade carrier between positions in which the blade is exposed for use and positions in which the guard covers the blade.

A holding catch is formed between the blade carrier and guard, the holding catch comprising the limit catch (26) on the outside of the bridge (21) that engages behind an inwardly directed formation (53) on the inside surface of the tubular guard at the front end of the slot (27). This inhibits the tubular guard from moving forwards whilst the scalpel is in use. However, a more forceful force needs to be countered by the manually operable stop (43).

The present invention therefore provides a scalpel blade accessory that may be supplied as such into the market. The scalpel blade accessory can be preassembled by introducing the blade carrier into the tubular guard with the longitudinally extending grooves (51) in cooperating relationship with the rails (52) provided in the tubular guard. Typically the pre-assembly would be conducted such that the blade carrier is in its most forward position relative to the tubular guard and projects somewhat out of the front end of the tubular guard as it would in the operative position. This makes it easy for a blade to be introduced into the blade carrier. Once a blade has been introduced, the scalpel blade accessory together with the blade can be installed on a standard blade handle in this position and immediately the tubular guard can be moved to its forward position in which it covers the blade and the scalpel is ready for use but in an inoperative condition.

The scalpel blade accessory may thus be used by individual surgeons to install their own choice of scalpel blades as and when required.

A scalpel blade accessory as provided by this invention may, of course, be packaged together with a specific scalpel blade, such as a carbon steel blade that may be in a separate corrosion protective packaging.

On the other hand, the scalpel blade accessory may be the fitted with a scalpel blade at a suitable fitments centre, optionally a factory producing the scalpel blade accessory or a site at which scalpel blades are produced, or a site at which scalpel cartridges are simply assembled for marketing into the marketplace. In this instance, the blade carrier and blade attached to it will be withdrawn into the tubular guard and the manually releasable locking catch (31) provided on the tubular guard will be in cooperation with the notch (32) on the blade carrier to releasably lock the tubular guard relative to the blade carrier in a position in which the tubular guard is fully extended and covers the blade. This locking catch operates to cause the lock to engage more firmly as the axial pressure is exerted on the blade and blade carrier, as will be clear from the above.

It is to be mentioned that the blade carrier is configured to guide the lug during the installation procedure so that the grooves in the sides of the lug become easily aligned with the edges of the narrower part of the slot in the blade. The handle is then pushed forwards until the rear end of the blade clicks into position over the rear end of the lug simultaneously disengaging the blade catch.

The scalpel can then be used as will be quite apparent to those skilled in the art by disengaging the manually releasable locking catch by operating the button and sliding the guard rearwards to expose the scalpel blade. It is to be noted that the blade is attached directly to the lug of the standard scalpel handle just as it would have been in the instance in which no guard or blade carrier were present.

Co-operation between the limit catch (26) on the bridge of the blade carrier and the inwardly directed formation (53) on the inside surface of the guard holds the guard in this operative position. The guard can be slid back into its operative position in which it covers the blade simply by urging the cover forwardly to overcome the resistance of the limit catch cooperating with the inwardly directed formation (53) on the inside surface of the guard. The arrangement thus provides a secure, effective and simple attachment. No costly custom made stainless steel handles need to be purchased.

In order to remove the scalpel blade cartridge from the handle, all that needs to be done is for the guard to be in its forward position with the locking catch engaged and the laterally movable release member (41) can be moved in order to move the blade carrier and blade slightly in a direction in which the rear end of the blade is moved off the rear end of the lug of the handle and the lug and the whole cartridge can be slid off the standard handle.

It will be understood that numerous variations may be made to the embodiment of the invention described above without departing from the scope hereof. In particular, the exact arrangement of the blade in the blade carrier can be varied widely so long as there is a facility to hold a blade captive relative to the blade carrier in the uninstalled condition and the lug of a standard scalpel handle can be engaged with the blade in generally conventional manner to provide a direct attachment of the blade to the handle.

Also, it is conceivable that the slightly inclined rear support face of the alignment face may be varied widely and in fact, depending on other constraints, the inclined face may not be necessary at all.

Still further, the scalpel blade accessory provided by the invention may be employed with the primary objective of it serving as a disposal device when a disposable scalpel blade has served its purpose.

There are thus a number of different ways in which a scalpel blade accessory according to the invention can be employed.

The invention claimed is:

1. A scalpel blade accessory comprising a scalpel blade carrier and a tubular guard slidable over the scalpel blade carrier between a retracted position in which the blade carrier is positioned to expose any blade associated with it for use and an extended position in which the guard covers the blade carrier and any such blade, the scalpel blade carrier being configured for receiving in cooperating relationship a scalpel blade for attachment to a scalpel handle for use, wherein the scalpel blade carrier has an alignment face for cooperation with a side face of a scalpel blade and at least one opening providing access through the alignment face to a position corresponding to that in which a mounting slot of any scalpel blade is to be located when a blade is attached to the blade carrier, wherein the blade carrier has a bridge spanning the alignment face so as to provide space for a scalpel blade between the alignment face and the bridge and wherein the bridge supports a blade catch positioned to cooperate with a rear end of a mounting slot of a scalpel blade to hold a relevant scalpel blade captive relative to the blade carrier in the absence of any scalpel handle, wherein the blade catch and the alignment face are such that the blade catch is disengagable from a position corresponding to registration with the rear end of the mounting slot of a scalpel blade consequent on engagement between the blade and a lug of a standard scalpel handle when the blade carrier and a blade carried thereby are assembled onto such a handle, in use.

2. A scalpel blade accessory as claimed in claim 1 in which the blade catch is moulded integral with the bridge and is located at a free end of an arm extending at right angles to the bridge in the general direction of movement of the blade carrier relative to the tubular guard.

3. A scalpel blade accessory as claimed in claim 1 in which the cross-sectional shape of the blade carrier and the tubular guard provides a stop that limits movement of the tubular guard relative to the blade carrier in the direction corresponding to retraction of the guard relative to the blade carrier.

4. A scalpel blade accessory as claimed in claim 1 in which a limit catch is provided on one of the blade carrier and the tubular guard to co-operate with a formation on the other of the tubular guard and the blade carrier to limit movement of the blade carrier relative to the tubular guard in a direction corresponding to the extended position in which the tubular guide covers the blade carrier.

5. A scalpel blade accessory as claimed in claim 1 in which a manually releasable locking catch is provided on the tubular guard with a cooperating notch being provided on the blade carrier to releasably lock the tubular guard relative to the blade carrier in a position in which the tubular guard is fully extended and covers the blade carrier and any blade carried thereby.

6. A scalpel blade accessory as claimed in claim 5 in which the manually releasable locking catch is such that the locking catch is urged into tighter engagement with the notch during the application of longitudinal force to the blade carrier in a direction corresponding to the installation of a scalpel blade onto the lug of a scalpel handle.

7. A scalpel blade accessory as claimed in claim 1 in which a rear end region of the blade carrier is provided with a laterally movable release member for operatively urging the rear end of the blade carrier and thus any blade carried by it out of engagement with a lug of a supporting scalpel handle in order to remove the blade and accessory therefrom.

8. A scalpel blade accessory as claimed in claim 7 in which the release member is configured such that its rear end in the fully retracted condition of the tubular guard on the blade carrier is in cooperating relationship with a manually operable stop located on one side of the tubular guard wherein the stop can be urged against a resiliency that biases it to its normal relaxed condition, to cooperate with the rear end of the release member and prevent it from moving rearwards relative to the tubular guard.

9. A scalpel blade accessory as claimed in claim 7 in which the release member at its forward end cooperates with a reduced size of passage within the tubular guard constituting a change in the cross-sectional shape of the blade carrier and the tubular guard to provide a stop limiting relative movement of the tubular guard relative to the blade carrier in a direction corresponding to retraction of the tubular guard relative to the blade carrier.

10. A scalpel blade accessory as claimed in claim 1 in which the blade carrier has a slightly inclined rear support face forming part of the alignment face and configured to cooperate with the rear end of a scalpel blade to urge the rear end of the blade slightly in a direction away from an access face thereof in a manner that will still allow the rear end of the slot of a scalpel blade to cooperate with a lug of a scalpel handle, in use.

11. A scalpel blade accessory as claimed in claim 10 in which a terminal end of the rear support face has a transverse stop for cooperation with a rear end of a scalpel blade, in use.

12. A scalpel blade accessory as claimed in claim 1 in which a holding catch is formed between the blade carrier and the guard for holding the guard in a retracted position in which the blade carrier is in a position corresponding to a blade being exposed for use.

13. A scalpel blade accessory as claimed in claim 1 in which for the blade carrier and the guard have co-operating grooves and rails for guiding movement of the guard relative to the blade carrier with the blade carrier in substance supporting the guard.

14. A scalpel blade accessory as claimed in claim 1 in combination with a scalpel blade installed on the blade carrier to provide a scalpel blade cartridge with a rear end of a mounting slot of the blade in cooperating relationship with the blade catch such that the scalpel blade is held captive relative to the blade carrier.

* * * * *